United States Patent [19]
Oobayashi et al.

[11] Patent Number: 5,621,523
[45] Date of Patent: Apr. 15, 1997

[54] METHOD AND APPARATUS FOR MEASURING PARTICLES IN A FLUID

[75] Inventors: Koji Oobayashi, Hiroshima; Satohiko Takanashi; Muneharu Ishikawa, both of Tsukuba, all of Japan

[73] Assignee: Kowa Company Ltd., Japan

[21] Appl. No.: 407,283

[22] Filed: Mar. 20, 1995

Related U.S. Application Data

[63] Continuation of Ser. No. 112,621, Aug. 26, 1993, abandoned.

[30] Foreign Application Priority Data

Aug. 27, 1992 [JP] Japan ................................... 4-227683
Jun. 30, 1993 [JP] Japan ................................... 5-161315

[51] Int. Cl.⁶ ....................................................... G01N 15/02
[52] U.S. Cl. ........................... 356/336; 356/338; 356/339; 356/352
[58] Field of Search ..................................... 356/336, 338, 356/339, 352

[56] References Cited

U.S. PATENT DOCUMENTS

| | | | |
|---|---|---|---|
| 3,909,132 | 9/1975 | Barrett | 356/352 |
| 4,035,080 | 7/1977 | Yamaguchi | 356/446 |
| 4,071,298 | 1/1978 | Falconer | 356/336 |
| 4,195,931 | 4/1980 | Hara | 356/352 |
| 4,830,494 | 5/1989 | Ishikawa et al. | 356/336 |
| 5,041,779 | 8/1991 | Hales | 356/352 |
| 5,262,644 | 11/1993 | Maguire | 356/346 |
| 5,305,077 | 4/1994 | Grego et al. | 356/352 |

*Primary Examiner*—Frank Gonzalez
*Assistant Examiner*—Robert Kim
*Attorney, Agent, or Firm*—Adams & Wilks

[57] ABSTRACT

A particle-containing fluid in a sample cuvette is irradiated by a laser beam from a light source section. The scattered light thus produced passes through converging lenses and a mask and impinges on an etalon interferometer. The etalon only transmits scattered light (Rayleigh scattered light) that is of the same wavelength as the light emitted by the laser light source. The transmitted scattered light components impinges on a photomultiplier, and based on the intensity of the light a calculating section sorts the particles according to size and calculates the number of particles per unit flow amount, the particle size distribution and so forth. To enable adjustments to be made to compensate for the environmental dependency characteristics of the etalon, a control unit is provided which consists of a photodiode and mirrors.

13 Claims, 5 Drawing Sheets

METHOD AND APPARATUS FOR MEASURING PARTICLES IN A FLUID

This is a continuation application of parent application Ser. No. 08/112,621 filed Aug. 26, 1993 now abandoned.

BACKGROUND OF THE INVENTION

1. Field of the Invention

The present invention relates to a method and apparatus for measuring particles, and more particularly to a method and apparatus which utilizes the scattering characteristics of light scattering from a fluid and from particles in the fluid to measure the diameter and/or quantity of the particles.

2. Description of the Prior Art

Various methods are known for detecting particles contained in a fluid. In particular, techniques using scattered light that permit such measurements to be carried out on an inline, continuous basis are applied in a broad range of fields. In semiconductor manufacturing processes in particular, the increasing density of large-scale integrated circuits (LSI) has increased the importance of cleaning technology for removing foreign particles that have adhered to wafers in the course of LSI fabrication.

However, the chemicals used on the wafers contain particles of foreign matter that can adhere to the wafer, giving rise to LSI malfunctions, short-circuits and other such problems. This being the case, it is necessary to reduce foreign particles in cleaning chemicals, so measuring the diameters or quantities of these particles in the fluids concerned has therefore become important.

A conventional measurement apparatus that utilizes scattered light detects particles contained in a fluid by projecting a beam of light at the fluid and measuring and analyzing the intensity of scattered light that is received, with no spectral separation of the scattered light being applied.

However, the scattered light thus measured includes light scattered by particles and light scattered by the fluid itself. The light scattered by the fluid has a strong background effect that makes it increasingly difficult to detect particles as the size of the particles decreases.

SUMMARY OF THE INVENTION

The object of the present invention is to provide a particle measurement apparatus that separates light scattered by the fluid from light scattered by the particle-containing fluid to thereby permit the background effect of light scattered by the fluid to be eliminated, improving the signal-to-noise (S/N) ratio and enabling the particles to be detected with good precision.

In accordance with the present invention, the above object is attained by an apparatus for measuring the diameter and/or quantity of particles in a fluid by receiving light scattered by the particles in the fluid, comprising separation means that separates out light that has been scattered by the fluid from light scattered from the particle-containing fluid irradiated with light projected from a light source, and calculating means for calculating the diameter and/or quantity of particles in the fluid based on the intensity of the extracted scattered light components.

In accordance with the above arrangement, scattered light from a fluid that contains particles is subjected to spectrometry, which makes it possible to separate Rayleigh scattered light scattered by the particles and Brillouin scattered light scattered by the fluid. Of the scattered light thus separated, the component corresponding to light scattered by particles is measured and converted to an electrical signal which is used as a basis for calculating the quantity and diameter of the particles.

The arrangement of the invention enables the contribution of the light scattered by the fluid to be decreased, the particle scattered light intensity S/N ratio to be greatly improved, and particle measurement precision and sensitivity to be increased.

Moreover, an intermediate collimation system is used in which collimation is performed by an optical means. This enables the measurement field of view to be readily changed and the interference conditions of the Fabry-Perot interferometer or the like to be selected, facilitating the separation of Brillouin and Rayleigh scattered light components. This has a major effect, enabling the contribution of the light scattered by the fluid to be decreased, the particle scattered light intensity S/N ratio to be greatly improved, and particle measurement precision and sensitivity to be increased.

BRIEF DESCRIPTION OF THE DRAWINGS

The purposes and features of the present invention will become more apparent from a consideration of the following detailed description taken in conjunction with the accompanying drawings in which.

DETAILED DESCRIPTION OF THE PREFERRED EMBODIMENTS

Figure 1:
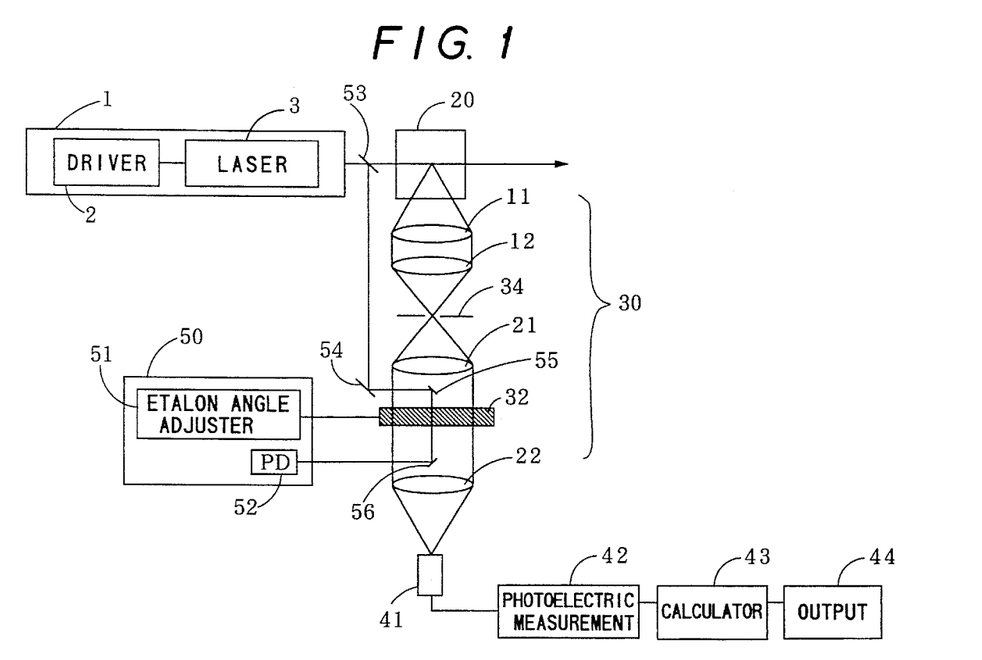
FIG. 1 is an explanatory drawing showing the general arrangement of a particle measurement apparatus using an etalon interferometer according to this invention.

Details of the present invention will now be described with reference to the embodiment illustrated in the drawings. FIG. 1 is a block diagram showing the general arrangement of a particle measurement apparatus according to this invention.

The apparatus comprises a sample cuvette 20, a spectroscopic section 30, a photodetecting section 41, a photoelectric measurement section 42, a calculating section 43, and an output section 44.

In the arrangement shown in FIG. 1, the spectroscopic section is an etalon interferometer 30 that is arranged to receive scattered light at a scattering angle of 90 degrees. A control unit 50 is attached to the part containing an etalon element 32 to compensate for the temperature-dependency of the refractive index profile of the etalon element 32.

The sample cuvette 20 is irradiated by a laser beam from a light source section 1 constituted by a laser light source 3 using for example a He-Ne laser, and a drive section 2. Scattered light from the particle-containing fluid is converged by collecting lens 11 and re-imaged by imaging lens 12. A field aperture 34 is disposed at the image plane to limit the measurement field of view.

This limiting of the measurement field determines the amount of fluid measured per unit time. This defining of the measurement field by the field aperture 34 can also be used to determine the interference conditions that apply when light impinges on the etalon interferometer.

In this embodiment, the field aperture 34 is a 100-micrometer pinhole. Making the pinhole larger can cause a Haidinger interference fringe to form, degrading the separation of Brillouin scattered light and Rayleigh scattered light. Therefore a size of pinhole is selected for the field aperture 34 that will not give rise to a Haidinger interference fringe. Using such a setting enables Brillouin scattered light and Rayleigh scattered light to be efficiently separated.

Scattered light from the field of view selected by means of the field aperture 34 is collimated by the collimating lens 21 and impinges on the etalon 32.

Having non-collimated scattered light impinge on the etalon 32 would also give rise to a Haidinger interference fringe, thereby degrading the separation of the Brillouin and Rayleigh scattered light, and therefore the collimating lens 21 is used to collimate the light, which has the effect of facilitating the separation of the Brillouin and Rayleigh scattered light.

The etalon 32 transmits only the scattered light (Rayleigh scattered light) whose frequency is equal to the frequency of light emitted from the laser light source 3.

The light thus spectrally separated through the etalon 32 is converged by the converging lens 22 and forms an image on the photoelectric surface of the photomultiplier 41. The angle of the etalon 32 is set so that Rayleigh scattered light is transmitted toward the photomultiplier 41.

As air temperature and other such changes can alter the refractive index of the etalon 32, changing the transmission frequency, a control unit 50 consisting of an etalon angle adjuster 51, a photodiode 52 and mirrors 53 to 56 is provided to enable this kind of dependency on surrounding environmental conditions to be compensated for.

Specifically, mirrors 53 to 55 are used to split off a reference laser beam from the beam output by the laser light source 3 and direct the reference laser beam onto a portion of the etalon 32. The beam emerging from the etalon 32 is received by the photodiode 52 via the mirror 56 and the etalon angle adjuster 51 is used to adjust the angle of the etalon 32 to maximize the amount of laser light that is transmitted. It is preferable to adjust the optical axes of the scattered light and reference laser beam beforehand so that the angle of maximum transmission of the reference beam coincides with the angle of maximum transmission of the Rayleigh scattered light. Allowing variation in the conditions of the surrounding environment to be compensated for in this way makes it possible to perform continuous measurements over an extended period of time with good stability.

The Rayleigh scattered light separated by the etalon 32 is converted into electrical information by the photomultiplier 41. A pulse or analog measurement of signals output by the photomultiplier 41 is performed by the photoelectric measurement section 42 to convert the signals into information that can be processed by the calculating section 43. The intensity of the signals thus measured is used by the calculating section 43 to sort particles according to size and to calculate the number of particles per unit flow and the particle size distribution, and this data is then output by the output section 44 consisting of a printer, display means and the like.

The advantages of thus subjecting the scattered light to spectrometry will now be described.

Light scattered by particles is mainly Rayleigh scattered light and has the same frequency as the incident light. Scattering produced by a fluid is mainly Rayleigh and Brillouin scattering. As in the case of light scattered from particles, Rayleigh scattered light arising from the fluid has the same frequency as the incident light. Spectral analysis shows that the frequency of Brillouin scattering components has a doublet spectral structure in which there is a slight shift from the frequency of the incident light. If $\lambda_0$ is the wavelength of the incident light in a vacuum, n is the refractive index of the fluid, Vs the velocity of sound in the fluid and $\theta$ the scattering angle, the degree of the shift $\Delta\omega$ can be expressed by $$\Delta\omega = |\omega_B - \omega_R| = \left| \frac{2 \cdot n}{\lambda_0} \cdot \sin\frac{\Theta}{2} \cdot V_S \right|$$

where $\omega_B$ is the Brillouin scattering frequency and $\omega_R$ is the Rayleigh scattering frequency.

Figure 5:
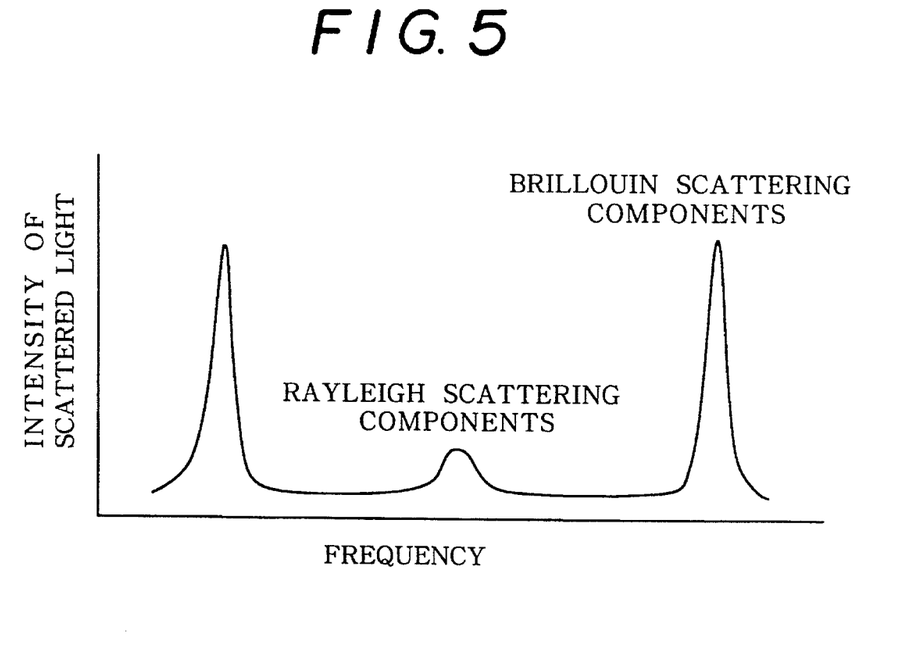
FIG. 5 is a spectrum of the Rayleigh and Brillouin scattered light components produced by water.

Taking water as an example, the spectrum thereof has the type of structure shown in FIG. 5. The wavelength of the incident light in a vacuum is assumed to be 632.8 nm. In water at 20° C., the refractive index is 1.3330 with respect to light of wavelength 589.3 nm, and the velocity of sound is 1500 m/s. With a scattering angle of 90 degrees, the extent of the Brillouin shift will be 4.5 GHz. Rayleigh and Brillouin scattering components can thus be separated by spectrometry. The Brillouin shift can be increased by increasing the scattering angle, facilitating the separation of Rayleigh and Brillouin scattering components.

The intensity ratio of the Rayleigh scattering component $I_R$ to the Brillouin scattering component $I_B$ is known as the Landau-Placzek ratio and can be expressed by $$\frac{I_R}{2 \cdot I_B} = \frac{C_P}{C_V} - 1$$

in which Cp denotes specific heat at constant pressure and Cv denotes specific heat at constant volume. In the case of water at 20° C. in which the specific heat at constant pressure Cp is 75.2688 J/g·K and the specific heat at constant volume Cv is 75.2400 J/g·K, the intensity ratio would be approximately 1:145. That is, the background produced by the water can be reduced to one-145th the level and the S/N ratio thereby improved.

The following effect can be obtained using an etalon as the spectroscopic means.

$B_n$ will be used to denote the intensity of the water background and $P_n$ the particle scattered light intensity when an etalon is not used. Similarly, $B_e$ will be used to denote the intensity of the water background and $P_e$ the particle scattered light intensity when an etalon is used. It is assumed that the etalon has been set to optimize the transmission of Rayleigh scattered light.

Figure 6:
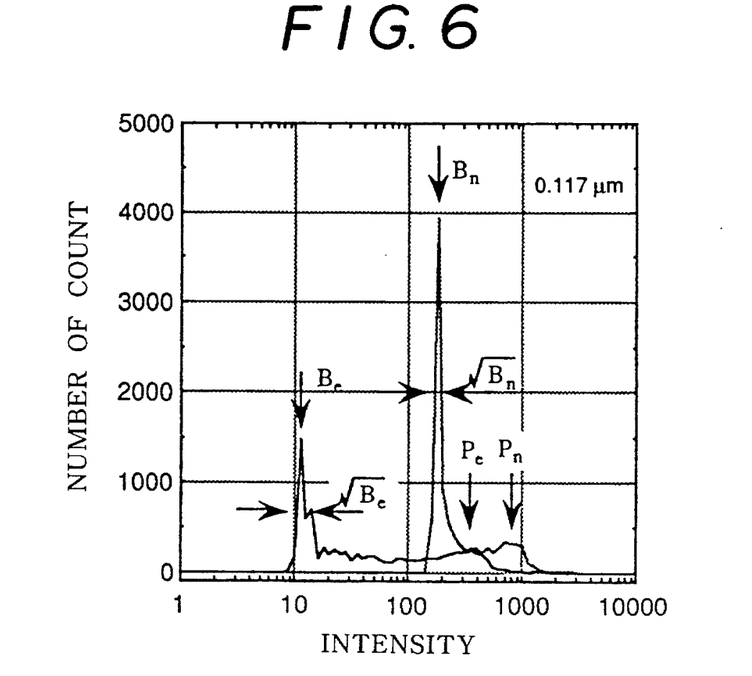
FIG. 6 is an explanatory drawing showing the water background reduction effect provided by an etalon.

This will produce the type of relationship shown by FIG. 6. The scattered light scattered by particles that is measured has been attenuated by an amount corresponding to the transmission factor of the etalon. Light scattered by the water is almost all Brillouin scattering comprised of components having a frequency that has undergone a slight shift from the frequency of Rayleigh scattered light. Brillouin scattering components arising from the water itself can be eliminated by using an etalon setting that optimizes the transmission of Rayleigh scattered light. As shown by FIG. 6, using the etalon markedly reduces the water scattered light components. This background reducing effect will be referred to as etalon effect E. Assuming that fluctuations in the scattered light intensity follow a Poisson distribution, the evaluation of the S/N ratio can be expressed by $$\frac{P_n}{\sqrt{B_n}} \geq \Delta$$

in which $\Delta$ represents the S/N ratio required to recognize the smallest particle that can be measured.

To study the effect of using an etalon, if $\Delta$ is also used to represent the S/N ratio required to recognize the smallest particle that can be measured when an etalon is not used, the S/N ratio can be expressed by $$\frac{P_e}{\sqrt{B_e}} \geq \Delta$$

The etalon effect can be expressed in the form of the following equation, in which $\alpha$ is the transmission factor of the etalon.

$$E = \frac{B_e}{B_n} \cdot \frac{1}{\alpha}$$

Concerning the smallest measurable particle, rewriting the above equation to take the etalon effect into account gives $$\frac{P_n}{\sqrt{B_n}} = \frac{P_e}{\sqrt{B_e}}$$

$$\frac{P_n^2}{P_e^2} = \frac{B_n}{B_e} = \alpha \cdot E$$

$$P_e = \sqrt{\alpha \cdot E} \cdot P_n$$

Taking into consideration the effect the etalon transmission factor has on, $P_e$ is related to the intensity $P_e'$ that should be used for comparison with $P_n$:

$$P_e = \alpha \cdot P_3'$$

Therefore $$P'_e = \sqrt{\frac{E}{\alpha}} \cdot P_n$$

Assuming that scattering from particles is Rayleigh scattering, the change in measurable particle size resulting from the use of an etalon is $$S_e = \sqrt[12]{\frac{E}{\alpha}} \cdot S_n$$

In accordance with the theoretical calculation, with an etalon effect of $E=1/145$ and $\alpha=1$, based on the above equations the minimum particle diameter that can be measured using an etalon is $$S_e = 0.66 \times S_n.$$

If $S_n=0.079$ micrometers, the minimum measurable particle diameter when an etalon is used will therefore be $$S_e = 0.052 \text{ micrometers}.$$

This means that incorporating an etalon into an apparatus able to measure a minimum particle diameter of 0.079 micrometers will enable the apparatus to measure a minimum particle diameter of 0.052 micrometers.

Figure 2:
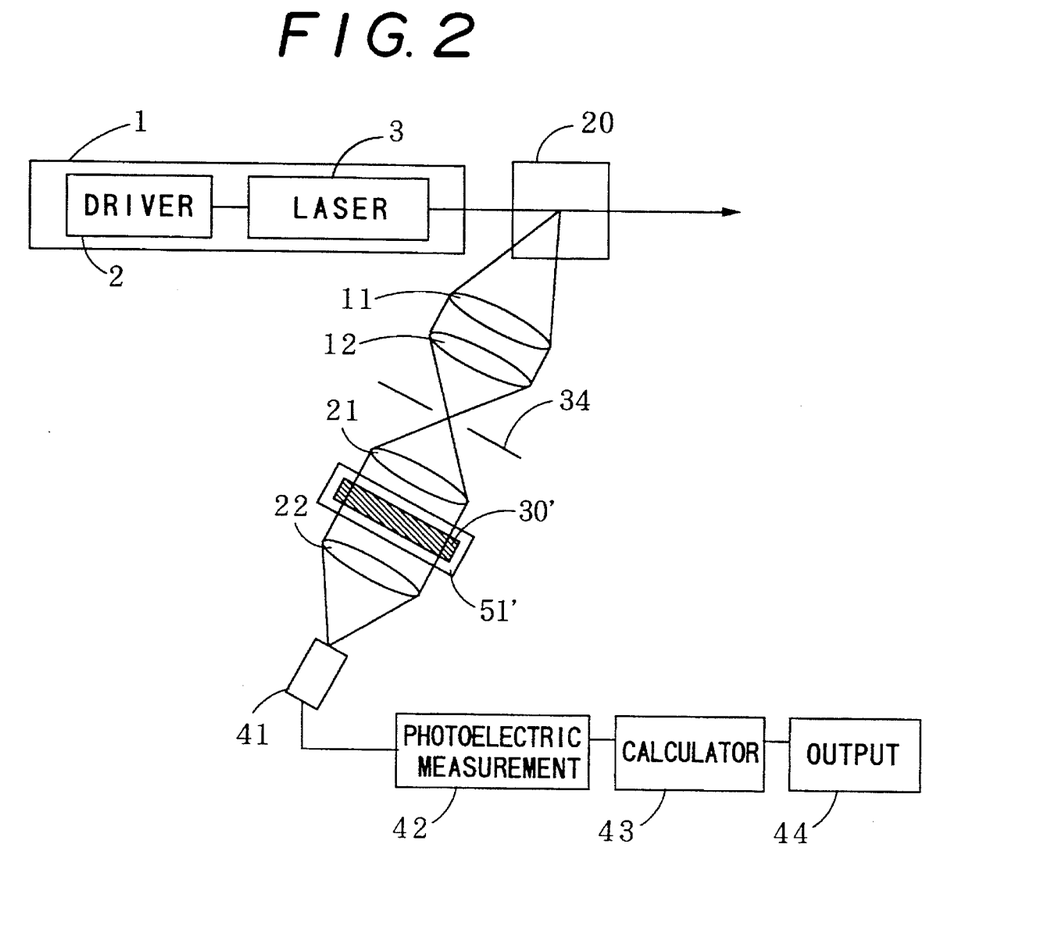
FIG. 2 is an explanatory drawing showing the general arrangement of a particle measurement apparatus using a Fabry-Perot interferometer according to this invention.

FIG. 2 shows an arrangement in which the spectroscopic section is a Fabry-Perot interferometer arranged to receive back-scattered light.

With reference to FIG. 2, the Fabry-Perot interferometer 30' is aligned in an isotherm chamber 51' to compensate for temperature-dependency. This arrangement ensures reliable measurement of Rayleigh scattering components with a Fabry-Perot interferometer, even when temperature variations or the like causes fluctuations in the amount of the shift in the Brillouin scattered light frequency.

Moreover, receiving back-scattered light enables the amount of the Brillouin shift to be increased, thereby facilitating the separation of Rayleigh and Brillouin scattered light components.

In the above embodiment the setting condition is selected that will not give rise to the Haidinger interference fringes. However, a mask can be used to spatially separate the Rayleigh scattering components in the Haidinger interference fringes, as described below. Because of the large image area measured by the optical system of the following embodiment, Haidinger interference fringes form on the photomultiplier surface and Rayleigh scattered light and Brillouin scattered light alternatively about a center formed by the light axis. Using a mask for spatial separation thereof makes it possible to measure just Rayleigh scattering.

Figure 3:
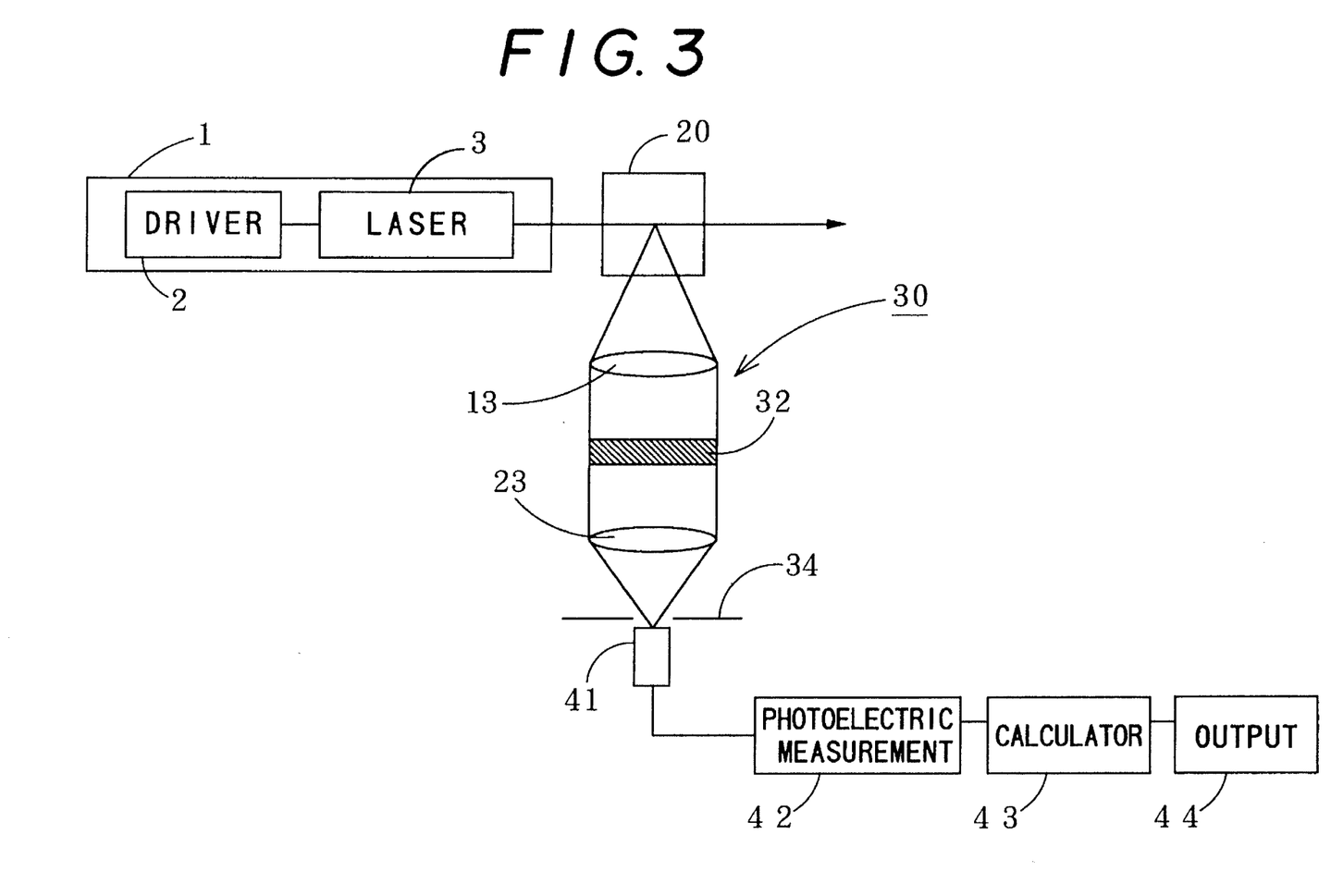
FIG. 3 is an explanatory drawing showing the general arrangement of a particle measurement apparatus using an etalon interferometer according to the invention.

The apparatus shown in FIG. 3 consists of a light source section 1 constituted by a laser light source 3 and a drive section 2 that drives the laser light source 3, a sample cuvette 20 of water or other such fluid containing the particles to be measured, an etalon interferometer 30 as the spectroscopic section, and measurement processing section constituted by a photomultiplier 41, photoelectric measurement section 42, calculating section 43 and output section 44.

FIG. 3 shows a configuration in which the etalon interferometer used as the spectroscopic section is arranged to receive scattered light at a scattering angle of 90 degrees.

The laser light source 3 uses a He-Ne laser to irradiate the sample cuvette 20.

Scattered light from the particle-containing fluid is guided to the etalon 32 via the collimating lens 13 of the etalon interferometer 30. The divergent scattered light is collimated by the collimating lens 13 into a parallel beam that impinges on the etalon 32.

Light that passes through the etalon 32 is converged by the converging lens 23, passes through a mask 34 and impinges on the photomultiplier 41.

The etalon 32 is set so that Rayleigh scattered light components corresponding to the frequency of the laser light source 3 are spectrally separated in the neighborhood of the axis of the light beam while other components are separated to the peripheral region. If the characteristics of the particles and the fluid, the frequency of the laser light source 3 and so forth are known beforehand, the spectroscopic characteristics of the etalon 32 can be set accordingly.

At the image-formation plane of the photomultiplier 41, the portion of the light near the beam axis corresponding to the Rayleigh scattered light component is extracted by means of the mask 34.

The Rayleigh scattered light components thus separated are converted to electric current by the photomultiplier, and photoelectric measurement section 42 is used to obtain a pulse or analog measurement of signals output by the photomultiplier 41 to generate a Rayleigh scattered light component intensity signal.

At the calculating section 43, which consists of a microcomputer or the like, the intensity of the signals measured by the photoelectric measurement section 42 is used to sort the particles according to size and to calculate the number of particles per unit flow, particle size distribution and the like. This data is output by the output section 44, which may consist of a CRT or other such display device, a printer, and an external storage device to store the data.

Figure 4:
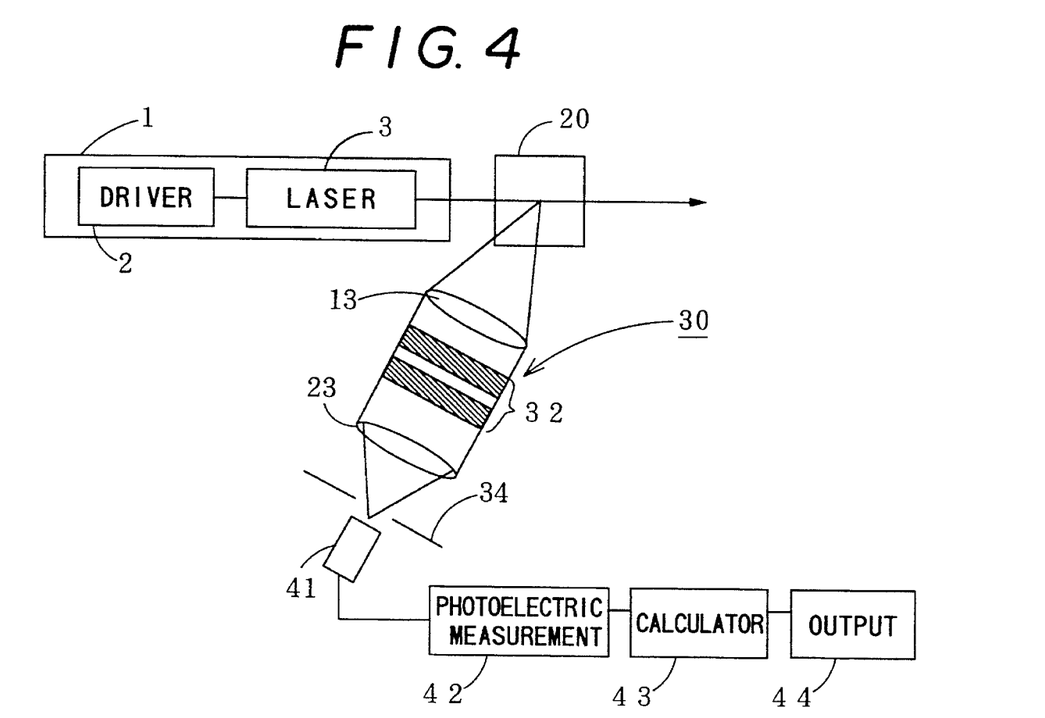
FIG. 4 is an explanatory drawing showing the general arrangement of a particle measurement apparatus using a Fabry-Perot interferometer according to the invention.

FIG. 4 shows another embodiment of the invention in which a Fabry-Perot interferometer 30" having a pair of mirrors 32' is used instead of the etalon interferometer 30 in FIG. 3. It functions in the same manner as in the embodiment in FIG. 3. This Fabry-Perot interferometer 30" is, however, arranged to receive back-scattered light, so that the amount of the Brillouin shift can be increased as in the embodiment in FIG. 2, thereby facilitating the separation of Rayleigh and Brillouin scattered light components.

While the invention has been described with reference to a preferred embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention should not be limited to the particular embodiment disclosed as the best mode contemplated for carrying out the invention, but that the invention will include all embodiments falling within the scope of the appended claims.

What is claimed is:

1. An apparatus for measuring particles in a fluid by irradiating the particle-containing fluid with a light from a light source and analyzing the light scattered by the particles to measure at least one of the diameter and quantity of the particles in the particle-containing fluid, comprising: interferometer means for receiving light scattered from the particle-containing fluid and for separating therefrom Rayleigh scattered light components scattered by the particles in the fluid from Brillouin scattered light components scattered by the fluid and corresponding to background light, the interferometer means including means for extracting the Rayleigh scattered light components and for eliminating the Brillouin scattered light components; calculating means for calculating at least one of the diameter and quantity of particles in the particle-containing fluid based on the intensity of only the extracted Rayleigh scattered light components; and adjustment and control means connected to the interferometer means for controlling the amount of light that is transmitted by the interferometer means.

2. An apparatus for measuring particles in a fluid by irradiating the particle-containing fluid with a light from a light source and analyzing the light scattered by the particles to measure at least one of the diameter and quantity of the particles in the particle-containing fluid, comprising: interferometer means for receiving light scattered from the particle-containing fluid and for separating therefrom Rayleigh scattered light components scattered by the particles in the fluid from Brillouin scattered light components scattered by the fluid and corresponding to background light, the interferometer means including means for extracting the Rayleigh scattered light components and for eliminating the Brillouin scattered light components; calculating means for calculating at least one of the diameter and quantity of particles in the particle-containing fluid based on the intensity of only the extracted Rayleigh scattered light components; and adjustment and control means connected to the interferometer means for controlling the amount of light that is transmitted by the interferometer means, the adjustment and control means comprising a photodiode for receiving light from the light source passing through the interferometer means, a plurality of mirrors for directing the light from the light source to the photodiode, and an angle adjuster for adjusting the angle of the interferometer means to control the amount of light that is transmitted by the interferometer means to a maximum amount.

3. An apparatus for measuring particles in a fluid by irradiating the particle-containing fluid with a light from a light source and analyzing the light scattered by the particles to measure at least one of the diameter and quantity of the particles in the particle-containing fluid, comprising: light collecting means for collecting light scattered by the particle-containing fluid; image means for imaging the collected scattered light; limiting means for limiting the field of view and for preventing the generation of interference fringes; collimating means for collimating scattered light from the field of view; interferometer means for receiving the collimated scattered light and for separating therefrom Rayleigh scattered light components scattered by the particles in the fluid from Brillouin light scattered by the fluid and corresponding to background light; light converging means for converging the scattered light separated by the interferometer means; adjustment and control means connected to the interferometer means for controlling the amount of light that is transmitted by the interferometer means; and calculating means for calculating at least one of the diameter and quantity of particles in the particle-containing fluid based on the intensity of the Rayleigh scattered light components.

4. An apparatus according to claim 3; wherein the interferometer means includes means for extracting the Rayleigh scattered light components having the same frequency as the source light, and for eliminating the Brillouin scattered light components corresponding to the background light.

5. An apparatus for measuring particles in a fluid by irradiating the particle-containing fluid with a light from a light source and analyzing the light scattered by the particles to measure at least one of the diameter and quantity of the particles in the particle-containing fluid, comprising: light collecting means for collecting light scattered by the particle-containing fluid; image means for imaging the collected scattered light; limiting means for limiting the field of view and for preventing the generation of interference fringes; collimating means for collimating scattered light from the field of view; interferometer means for receiving the collimated scattered light and for separating therefrom Rayleigh scattered light components scattered by the particles in the fluid from Brillouin light scattered by the fluid and corresponding to background light; light converging means for converging the scattered light separated by the interferometer means; adjustment and control means connected to the interferometer means for controlling the amount of light that is transmitted my the interferometer means, the adjustment and control means comprising a photodiode for receiving light from the light source passing through the interferometer means, a plurality of mirrors for directing the light from the light source to the photodiode, and an angle adjuster for adjusting the angle of the interferometer means to control the amount of light that is transmitted by the interferometer means to a maximum amount; and calculating means for calculating at least one of the diameter and quantity of particles in the particle-containing fluid based on the intensity of the Rayleigh scattered light components.

6. A method for measuring particles in a fluid by irradiating the particle-containing fluid with a light from a light source and analyzing the light scattered by the particles to measures at least one of the diameter and quantity of the particles in the particle-containing fluid, comprising the steps of:

irradiating a particle-containing fluid with light to product Rayleigh scattered light components attributable to the particles and Brillouin scattered light components attributable to the fluid;

using an interferometer means to separate the Rayleigh scattered light components attributable to the particles from the Brillouin scattered light components attributable to the fluid;

adjusting and controlling the amount of light that is transmitted by the interferometer means to a maximum amount; and calculating at least one of the diameter and quantity of particles in the particle-containing fluid based on the intensity of only the separated Rayleigh scattered light components.

7. An apparatus for measuring particles in a fluid by irradiating the particle-containing fluid with a light from a light source and analyzing the light scattered by the particles to measure at least one of the diameter and quantity of particles in the particle-containing fluid, comprising: means comprising an interferometer for receiving light scattered from the particle-containing fluid and for separating therefrom Rayleigh scattered light components scattered by the particles in the fluid from Brillouin scattered light components scattered by the fluid and corresponding to background light; means connected to the interferometer for controlling the amount of light that is transmitted by the interferometer; and calculating means for calculating at least one of the diameter and quantity of particles in the particle-containing fluid based on the intensity of only the separated Rayleigh scattered light components.

8. An apparatus for measuring particles in a fluid by irradiating the particle-containing fluid with a light from a light source and analyzing the light scattered by the particles to measure at least one of the diameter and quantity of the particles in the particle-containing fluid, comprising:

interferometer means for receiving light scattered from the particle-containing fluid and for separating therefrom Rayleigh scattered light components scattered by the particles in the fluid from Brillouin scattered light components scattered by the fluid and corresponding to background light;

means for guiding the light from the light source through the interferometer means;

adjustment and control means connected to the interferometer means for controlling the amount of light that is transmitted by the interferometer means to a maximum amount; and calculating means for calculating at least one of the diameter and quantity of particles in the particle-containing fluid based on the intensity of only the separated Rayleigh scattered light components.

9. An apparatus according to claim 8; further comprising means for limiting the field of view of the Rayleigh and Brillouin scattered light components and preventing the generation of interference fringes.

10. An apparatus for measuring particles in a fluid by irradiating the particle-containing fluid with a light from a light source and analyzing the light scattered by the particles to measure at least one of the diameter and quantity of the particles in the particle-containing fluid, comprising:

interferometer means for receiving light scattered from the particle-containing fluid and for separating therefrom Rayleigh scattered light components scattered by the particles in the fluid from Brillouin scattered light components scattered by the fluid and corresponding to background light;

means for guiding the light from the light source through the interferometer means;

adjustment and control means connected to the interferometer means for controlling the amount of light that is transmitted by the interferometer means to a maximum amount, the adjustment and control means comprising a photodiode for receiving the light from the light source passing through the interferometer means and an angle adjuster for adjusting the angle of the interferometer means to control the amount of light that is transmitted by the interferometer to a maximum amount; and calculating means for calculating at least one of the diameter and quantity of particles in the particle-containing fluid based on the intensity of only the separated Rayleigh scattered light components.

11. A method for measuring particles in a fluid by irradiating the particle-containing fluid with a light from a light source and analyzing the light scattered by the particles to measure at least one of the diameter and quantity of the particles in the particle-containing fluid, comprising the steps of:

irradiating a particle-containing fluid with light to produce Rayleigh scattered light components attributable to the particles and Brillouin scattered light components attributable to the fluid;

using an interferometer means to separate the Rayleigh scattered light components attributable to the particles from the Brillouin scattered light components attributable to the fluid;

guiding the light from the light source through the interferometer means;

adjusting and controlling the amount of light that is transmitted by the interferometer means to a maximum amount; and calculating at least one of the diameter and quantity of particles in the particle-containing fluid based on the intensity of only the separated Rayleigh scattered light components.

12. A method according to claim 11; further comprising the step of limiting the field of view of the Rayleigh and Brillouin scattered light components to prevent the generation of interference fringes.

13. A method for measuring particles in a fluid by irradiating the particle-containing fluid with a light from a light source and analyzing the light scattered by the particles to measures at least one of the diameter and quantity of the particles in the particle-containing fluid, comprising the steps of:

irradiating a particle-containing fluid with light to produce Rayleigh scattered light components attributable to the particles and Brillouin scattered light components attributable to the fluid;

using an interferometer means to separate the Rayleigh scattered light components attributable to the particles from the Brillouin scattered light components attributable to the fluid;

adjusting and controlling the amount of light that is transmitted by the interferometer means to a maximum amount by using a photodiode to receive the light irradiated by the light source, and by using an angle adjuster to adjust the angle of the interferometer means to control the amount of light that is transmitted by the interferometer means to a maximum amount; and calculating at least one of the diameter and quantity of particles in the particle-containing fluid based on the intensity of only the separated Rayleigh scattered light components.

* * * * *